(12) United States Patent
Feda et al.

(10) Patent No.: US 6,480,567 B2
(45) Date of Patent: Nov. 12, 2002

(54) X-RAY PROBE SHEATH APPARATUS

(75) Inventors: Francis M. Feda, Maynard, MA (US); James Kelland, E. Walpole, MA (US)

(73) Assignee: Photoelectron Corporation, North Billerica, MA (US)

( * ) Notice: Subject to any disclaimer, the term of this patent is extended or adjusted under 35 U.S.C. 154(b) by 98 days.

(21) Appl. No.: 09/780,823

(22) Filed: Feb. 9, 2001

(65) Prior Publication Data

US 2001/0050971 A1 Dec. 13, 2001

Related U.S. Application Data (62) Division of application No. 09/208,964, filed on Dec. 10, 1998, now Pat. No. 6,245,047.

(51) Int. Cl.$^7$ ................................................ A61B 5/01
(52) U.S. Cl. ........................................ 378/65; 600/427
(58) Field of Search ............................. 600/427, 407; 378/65, 121; 604/20, 21, 192

(56) References Cited

U.S. PATENT DOCUMENTS

| | | | |
|---|---|---|---|
| 4,986,818 A | 1/1991 | Imbert et al. ............... | 604/192 |
| 5,090,043 A | * 2/1992 | Parker et al. ............... | 378/121 |
| 5,681,296 A | 10/1997 | Ishida ......................... | 604/282 |
| 5,830,188 A | 11/1998 | Abouleish ................... | 604/158 |
| 5,863,287 A | 1/1999 | Segawa ....................... | 600/121 |
| 5,865,721 A | 2/1999 | Andrews et al. ............. | 600/18 |
| 5,902,282 A | 5/1999 | Balbierz ..................... | 604/264 |
| 6,069,698 A | * 5/2000 | Ozawa et al. ............... | 356/511 |

\* cited by examiner

*Primary Examiner*—Brian L. Casler
*Assistant Examiner*—K. Sirmons
(74) *Attorney, Agent, or Firm*—McDermott, Will & Emery (57) ABSTRACT

The invention is directed toward an X-ray treatment kit to be used in an X-ray treatment apparatus. The X-ray treatment kit includes at least one of an improved biocompatible sheath or an improved probe, wherein an airflow path is maintained between the sheath and probe to allow air present within a void region of the sheath to escape as the probe is inserted therein. In various embodiments, the sheath includes a securing assembly which removably secures the sheath to the probe and provides an airflow path, e.g. an internally disposed annular ring with air shunts. Such a sheath may be used with a typical smooth probe to form an X-ray treatment kit. In other embodiments, an improved probe includes an air channel formed substantially along its length. In such a case, the improved probe may be used with a typical sheath, i.e., a sheath having a solid annular ring at its open end, to form an X-ray treatment kit.

11 Claims, 6 Drawing Sheets

FIG. 5

X-RAY PROBE SHEATH APPARATUS

CROSS-REFERENCE TO RELATED APPLICATIONS

This application is a divisional of application Ser. No. 09/208,964, now U.S. Pat. No. 6,245,047, entitled X-RAY PROBE SHEATH APPARATUS and filed Dec. 10, 1998.

STATEMENT REGARDING FEDERALLY SPONSORED RESEARCH

Not Applicable

REFERENCE TO MICROFICHE APPENDIX

Not Applicable

BACKGROUND OF THE INVENTION

This invention relates to a miniaturized, programmable radiation source having an x-ray emitting probe for use in delivering substantially constant or intermittent levels of x-rays to a specified region and, more particularly, to a biocompatible sheath, for covering the probe during treatment, or a biocompatible sheath and probe treatment kit.

In the field of medicine, radiation is used for diagnostic, therapeutic and palliative treatment of patients. The conventional medical radiation sources used for these treatments include large fixed position machines as well as small, transportable radiation generating probes. The current state of the art treatment systems utilize computers to generate complex treatment plans for treating complex geometric volumes.

Typically, these systems apply doses of radiation in order to inhibit the growth of new tissue because it is known that radiation affects dividing cells more than the mature cells found in non-growing tissue. Thus, the regrowth of cancerous tissue in the site of an excised tumor can be treated with radiation to prevent the recurrence of cancer. Alternatively, radiation can be applied to other areas of the body to inhibit tissue growth, for example the growth of new blood vessels inside the eye that can cause macular degeneration.

Conventional radiation treatments systems, such as the LINAC used for medical treatment, utilize a high power remote radiation source and direct a beam of radiation at a target area, such as tumor inside the body of a patient. This type of treatment is referred to as teletherapy because the radiation source is located at a predefined distance, typically on the order of one meter, from the target. This treatment suffers from the disadvantage that tissue disposed between the radiation source and the target is exposed to radiation.

Figure 1:
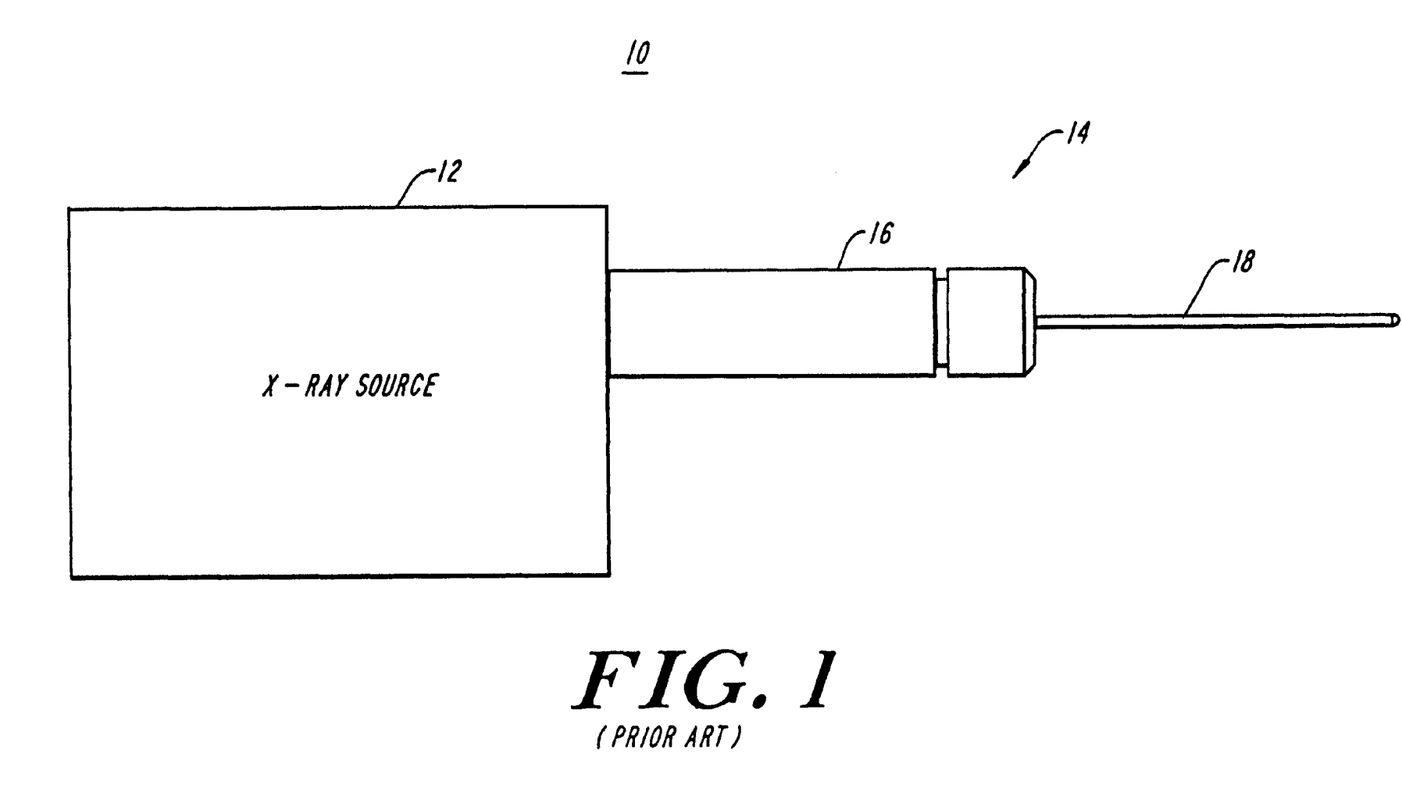
FIG. 1 is a diagrammatic view of an X-ray treatment system of the prior art.

An alternative treatment system utilizing a point source of radiation is disclosed in U.S. Pat. No. 5,153,900 ('900 patent) issued to Nomikos et al., owned by the assignee of the present application, which is hereby incorporated by reference. As shown in FIG. 1, the system 10 includes an x-ray source 12 and a miniaturized insertable probe assembly 14 capable of producing low power radiation in predefined dose geometries or profiles disposed about a predetermined location. The probe assembly 14 includes a shoulder 16 which provides a rigid surface by which the system 10 may be secured to another element, such as a stereotactic frame used in the treatment of brain tumors. The probe assembly 14 also includes an X-ray emitting tube 18, or "probe", rigidly secured to shoulder 16. This type of treatment is referred to as brachytherapy because the X-ray source is located close to or in some cases within the area receiving treatment. One advantage of brachytherapy is that the radiation is applied primarily to treat a predefined tissue volume, without significantly affecting the tissue in adjacent volumes.

Typical radiation therapy treatment involves positioning the insertable probe 18 into the tumor or the site where the tumor or a portion of the tumor was removed to treat the tissue adjacent to the site with a "local boost" of radiation. In order to facilitate controlled treatment of the site, it is desirable to support the tissue portions to be treated at a predefined distance from the radiation source. Alternatively, where the treatment involves the treatment of surface tissue or the surface of an organ, it is desirable to control the shape of the surface as well as the shape of the radiation field applied to the surface.

The treatment can involve the application of radiation, either continuously or intermittently, over an extended period of time. Therefore, in some cases, the insertable probe 18 is adjustably supported in a compliant manner to accurately position the radiation source with respect to the treated site and accommodate normal minor movements of the patient, such as movements associated with breathing.

Figure 2A:
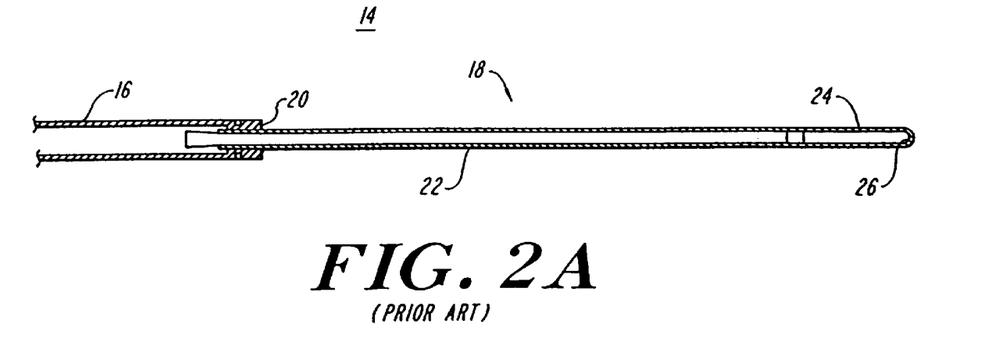
FIG. 2A is a diagrammatic cross-section side view of an X-ray emitting probe of the prior art.

It is typically considered essential that the interface between the patient and the probe 18 be biocompatible. However, the probes are not always made from such material. Rather, as disclosed in the '900 patent and shown in probe assembly 14 of FIG. 2A, the probe 18 is usually a hollow, evacuated cylinder made of a beryllium (Be) cap 24 at one end, a molybdenum-rhenium (Mo-Re), molybdenum (Mo) or mu-metal tubular body 22, and a probe shoulder 16 opposite the Be cap 24. The tubular body 22 is rigidly secured to the probe shoulder 16 using bushing element 20. A target assembly 26 is located inside the Be Cap 24 of probe 18 and emits x-rays in response to an incident electron beam produced from the x-ray source 12 of FIG. 1. The target assembly includes an x-ray emission element consisting, typically, of a small beryllium (Be) target element 26 located within the cap 24 and coated on the side exposed to the incident electron beam with a thin film or layer of a high-Z element, such as tungsten (W), uranium (U) or gold (Au). A typical probe of this type is 10–16 cm in length and has an inner diameter of about 2 mm and an outer diameter of about 3 mm.

Figure 2B:
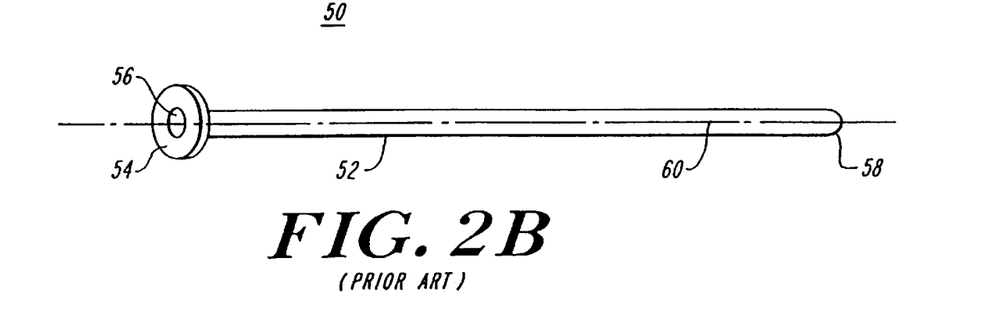
FIG. 2B is a diagrammatic view of a probe sheath of the prior art.
Figure 2C:
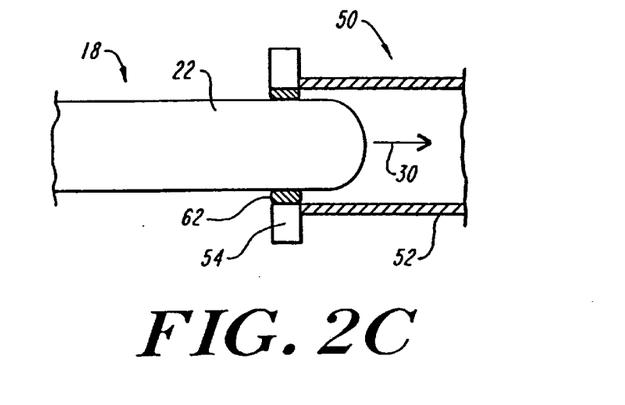
FIG. 2C is a cut-away side view of a probe being inserted into a sheath, in accordance with the prior art.

Probe 18 is comprised of materials which maximize the x-ray emitting characteristics of the device, rather than materials which concern themselves with biocompatibility. Therefore, a biocompatible sheath 50, shown in FIG. 2B, is typically used to encase the probe 18 during patient treatments. Such sheaths 50 are usually comprised of an elongated and cylindrical (assuming the probe to be cylindrical) body 52, very closely mimicking the dimensions of the probe 18. Additionally, a sheath 50 has a smooth hollow interior cavity defined by an inner surface of the sheath body 52 and a closed end 58 of the sheath 50. The diameter of the inner surface of the sheath is about 3.3 mm, and accommodates insertion of a probe having an outer diameter of about 3 mm, as described above. Opposite the closed end 58, is an open end 56, which accommodates insertion of the probe 18 within the sheath 50. Near the open end 56 of the sheath is a flange 54 and an annular ring 62, as shown in FIG. 2C. The circumferential outer surface of annular ring 62 is integral with the inner surface of sheath 50 and oriented within or near flange 54. The probe opening formed within annular ring 62 is about 2.9 mm, which accommodates insertion of a probe body 22 of diameter of about 3 mm into the sheath 50, in the direction of arrow 30. Annular ring 62 ultimately comes to rest, at the terminus of the probe's 18 insertion into the sheath 50, near the probe shoulder 16, thereby removably securing the sheath 50 to the probe 18. Because the diameter of the annular ring is less than the diameter of the probe body 22, annular ring 62 is made to be compliant relative to probe body 22. The compliance of the annular ring 62 causes the sheath 50 to securely grip probe 18, so that sheath 50 does not become easily removed from the probe 18 during use. To achieve the desired advantages of biocompatibility and a compressible securing assembly, sheath 50 is typically made out of an aliphatic thermoplastic material, for example, "Tecoflex®" (supplied by Thermedics Inc. of Waltham, Mass.).

A problem with typical sheaths is that as a result of the smaller inner diameter of annular ring 62, relative to the probe's outer diameter, and the location of the ring 62 at or near flange 54 of the sheath 50, air becomes trapped within the region between the sheath 50 and probe 18, as the probe 18 is inserted into the sheath 50, as shown in FIG. 2C. Therefore, it can be difficult to insert the probe within the sheath without exerting an undesirable amount of force on the probe and sheath combination, which could lead to bending of the probe. Additionally, there is an inability to fully seat the sheath on the probe due to the gas pressure at the closed end of the sheath which dislodges the sheath from the probe.

It is an object of the present invention to provide an X-ray treatment kit which includes a probe and sheath combination for use with an X-ray treatment apparatus, the combination allowing the escape of air existing between the probe and the sheath during insertion of the probe into the sheath.

It is a further object of the present invention to provide an improved sheath to be used with typical smooth probes, wherein the sheath provides an airflow path for the escape of air present between the probe and sheath during insertion of the probe into the sheath.

SUMMARY OF THE INVENTION

The above and other objects of the present invention are achieved by an X-ray treatment kit, including an improved sheath to be used with existing X-ray probes, or an improved probe to be used with typical sheaths. The improved sheath may take a variety of embodiments, but each embodiment must allow for the escape of air from the sheath as the probe is being inserted therein. Like prior art sheaths, the sheath embodiments of the present invention may be made from a thermoplastic material, such as Tecoflex®. The sheath is comprised of an elongated body extending along a central axis and having an elongated central void region extending between a closed end and an open end of the sheath. The sheath body has an inner surface which defines the central void region and a biocompatible outer surface. The sheath also includes a securing assembly that removably secures the sheath to the probe. In various embodiments, the securing assembly is positioned within the void region and is adapted for frictional engagement with the probe, while also providing an airflow path between the open end and a portion of the void region near the closed end. Optionally, the sheath may also include an X-ray source portion which encases the X-ray source, as well as the probe, and alleviates the need to sterilize the X-ray source for treatments.

In a first X-ray treatment kit embodiment, a sheath has an annular ring disposed within the void region and integral with the inner surface of the sheath. The annular ring serves as a securing assembly and includes cut-outs which form air shunts that define an airflow path between the sheath and the probe. The inner diameter of the annular ring is slightly less than the outer diameter of the probe. Additionally, the annular ring is compliant relative to the probe, to allow the ring to removably grip the probe. The annular ring having air shunts may be displaced anywhere within the void region and still achieve the desired objectives.

In a second X-ray treatment kit embodiment, a plurality of annular protrusions extend from the inner surface of the sheath, within the void region, and toward the sheath's central axis. In this embodiment, the protrusions take the form of "bullets" which are displaced about the inner surface of the sheath and secure the sheath to the probe, while also providing an airflow path along the length of the sheath. Other forms of protrusions may also be used and the displacement pattern varied, or the inner surface of the sheath may be extruded along some portion of its length so long as there are a sufficient number of annular protrusions to secure the probe within the sheath and there remains sufficient spacing between the protrusions to maintain an airflow path along the length of the sheath. As with the annular ring, the protrusions form an unobstructed opening within the sheath which is slightly less in diameter than the outer diameter of the probe. Therefore, the annular protrusions are made from a material which is compliant relative to the probe.

In a third X-ray treatment kit embodiment, a solid annular ring acts as the securing assembly and also facilitates the flow of air from the sheath when a probe is being inserted therein. In this embodiment, the annular ring is positioned near the closed end of the sheath and does not include the air shunts of the first embodiment. However, because the annular ring is positioned near the closed end of the sheath, air is not obstructed from flowing out of the open end of the sheath as the probe is inserted therein. Once again, the inner diameter of the annular ring is slightly less than the outer diameter of the probe and the annular ring is made of a sufficiently compliant material.

A fourth X-ray treatment kit embodiment includes an improved probe and a typical sheath having a smooth inner surface and an annular ring without air shunts disposed at the open end of the sheath. The probe includes an air channel formed along a substantial portion of its length, which may take a variety of forms. The air channel may take the form, for example, of a long straight channel, a spiral channel, or a series of mini air channels. However, the depth of the air channel must be such that it does not interfere with or adversely affect the transmission of electrons down the center of the probe to the target element. In another form, the probe may have a pitted or irregular surface for a substantial portion of its length, such that air channels are formed within the probe surface. With an X-ray treatment kit embodying an improved probe, the securing assembly of the sheath need not provide an airflow path.

BRIEF DESCRIPTION OF THE DRAWINGS

The foregoing and other objects of this invention, the various features thereof, as well as the invention itself, may be more fully understood from the following description, when read together with the accompanying drawings in which.

DETAILED DESCRIPTION OF THE PREFERRED EMBODIMENTS

The present invention is a sheath for use with an X-ray emitting probe and an X-ray treatment kit, comprised of an X-ray emitting tube, i.e., a probe, and a sheath, wherein the kit provides an airflow path for the escape of air present within the central void region of the sheath as the probe is inserted therein. The X-ray emitting kit may take a variety of embodiments, but each embodiment must allow for the escape of air from the sheath as the probe is being inserted therein. Various embodiments include an improved sheath which provides an airflow path or an improved probe which provides an airflow path. Of course, an improved sheath may be used with an improved probe, but the embodiments described herein allow for the use of either of an improved sheath or probe. As will be apparent when referring to the figures, when the same element is used unchanged in more than one figure, the element retains its previously assigned identifying numeral in subsequent figures. Also, the preferred embodiments include sheaths for cylindrical probes (i.e., circular cross-section) and kits with cylindrical probes. In alternate forms, probes having different cross-sections (e.g. polygonal, elliptical) may be used. Additionally, the various embodiments of the sheath may also include an X-ray source portion which encases a substantial portion or all of the X-ray source.

Like the prior art sheath, it is preferred that the sheaths of the various embodiments of the present invention described herein are constructed from an aliphatic polyurethane thermoplastic material, such as "Tecoflex®". Additionally, each sheath is comprised of an elongated body extending along a central axis and having an elongated central void region extending between a closed end and an open end of the sheath. The sheath body has an inner surface which defines the central void region and a biocompatible outer surface. The sheath also includes a securing assembly that removably secures the sheath to the probe. It is assumed, for illustrative purposes, that the probe has an outer diameter of about 3 mm and the principle portion of the sheath has an inner diameter of about 3.3 mm.

Figure 3A:
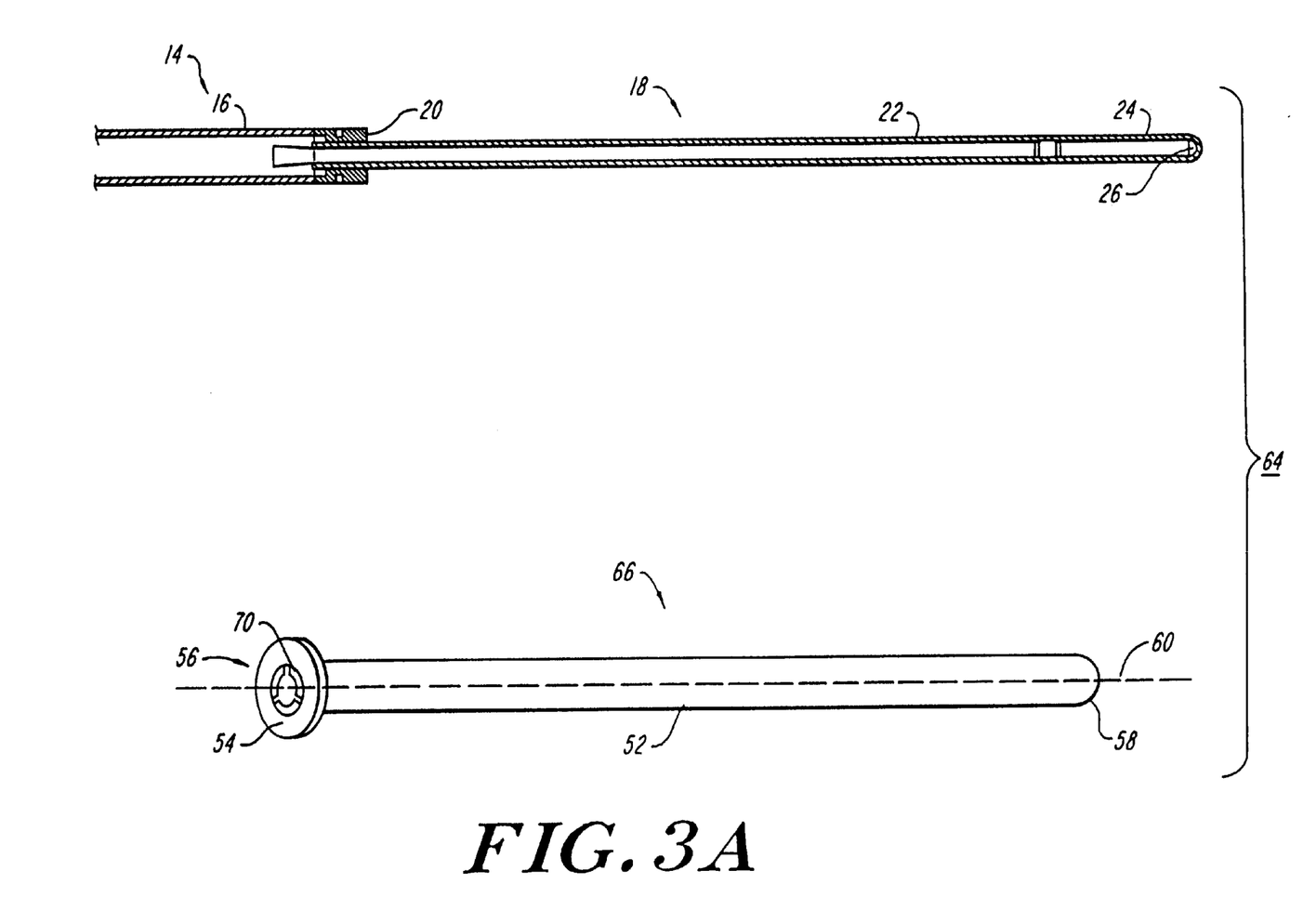
FIG. 3A is a diagrammatic cross sectional side view of an X-ray treatment kit, including an improved sheath in accordance with the present invention.

Referring to FIG. 3A, a first embodiment of an X-ray emitting kit 64 of the present invention includes an improved sheath 66 to be used with a typical probe 18, shown from a side view. As is shown, the open end 56 of sheath 66 is defined by an opening in flange 54. The sheath 66 is constructed to accommodate the insertion of probe 18 via opening 56 and along the central axis 60 of sheath 66. Once inserted, the X-ray emitting target assembly 26 of probe 18 is encased by the closed end 58 of the sheath 66. In this embodiment of the sheath, a securing assembly 70, in this case an annular ring, is used to frictionally engage, i.e., grip, probe 18 when the probe is inserted therein.

Figure 3B:
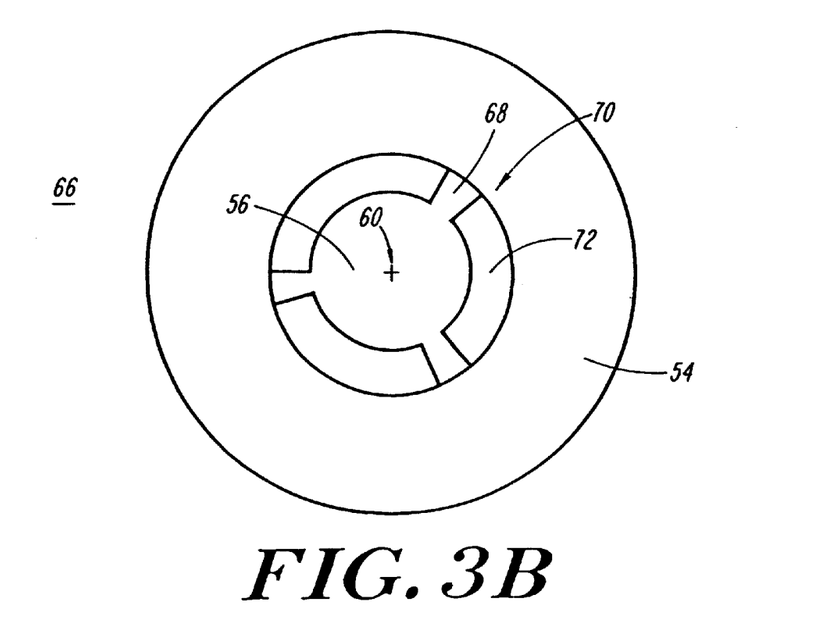
FIG. 3B is a diagrammatic rear view of the sheath of FIG. 3A.

Referring to FIG. 3B, securing assembly 70 of sheath 66 is in the form of an annular ring 72 having air shunts 68 formed by cutouts. While three such cutouts are illustrated, different numbers of cutouts may be used in other forms of the inventions. In this embodiment, annular ring 72 is disposed circumferentially within sheath 72 and about the sheath's inner surface. Annular ring 72 has a diameter which is slightly less than the diameter of probe 18 and is constructed to be compliant relative to probe 18. The inner diameter of annular ring 72 is about 2.9 mm, to accommodate insertion of a probe having an outer diameter of about 3 mm. It is preferred that annular ring 72 is constructed of an aliphatic polyurethane thermoplastic material, which is sufficiently compliant to grip probe 18. In this embodiment, annular ring 72 is disposed within the sheath's void region and integral with the sheath's inner surface proximate to flange 54, although it could alternatively be disposed anywhere within the void region of the sheath and still achieve the gripping function of the securing assembly while also providing an airflow path. The air shunts 68 create an airflow path between the sheath 66 and probe 18, which allows for the escape of air from the central void region of the sheath while the probe is being inserted therein. As a result, using the X-ray emitting kit 64 of this embodiment, air is not trapped within the sheath 66 as probe 18 is inserted therein. Once the probe is removed from sheath 66, the annular ring 72 decompresses and returns to take substantially its original form.

Figure 3C:
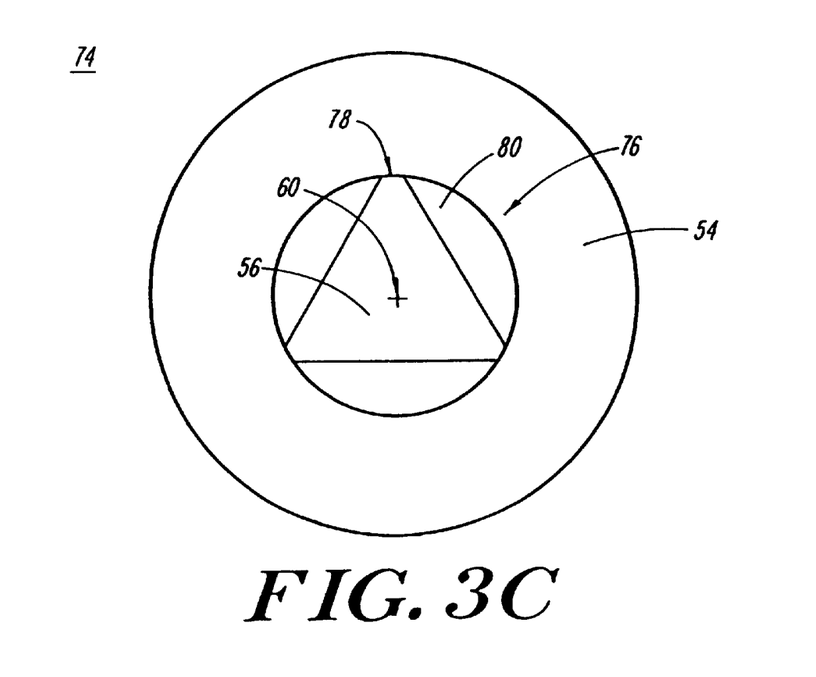
FIG. 3C is a diagrammatic rear view of a sheath having annular protrusions which establish line contacts with an inserted probe, in accordance with the present invention.

In the illustrated embodiment, the annular protrusions, i.e., the innermost surfaces, of the segments of ring 72 have an arcuate cross-section. As shown in FIG. 3C, other shapes may alternatively be used for a securing assembly 76. For example, sheath 74 of FIG. 3C includes annular protrusions 80 having planar surfaces extending perpendicular to a radius of the sheath, so that three "line contacts" may be made with an inserted probe 18. As is shown, air shunts 78 allow for the escape of air from the central void region of sheath 74 as probe 18 is inserted in opening 56.

Figure 4:
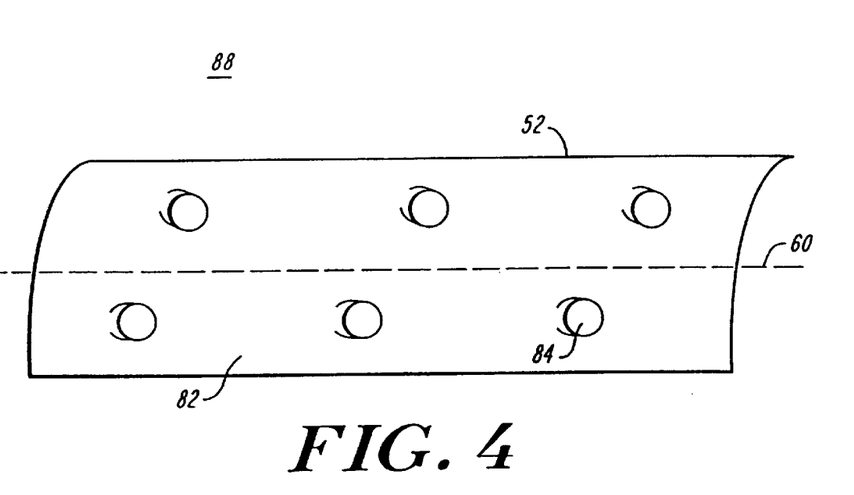
FIG. 4 is a cut-away side view of a portion of the interior surface of a sheath, as part of an X-ray emitting kit, having annular protrusions extending inwardly from the inner surface of the sheath.

Referring to FIG. 4, a second embodiment of an X-ray emitting kit includes an improved sheath 88 to be used with a typical probe 18, shown in FIG. 2B. Like previous sheaths, sheath 88 has an elongated body 52 extending along a central axis 60, as shown in part in FIG. 2B. The securing assembly of this sheath frictionally engages the probe and also maintains an airflow path between the open end 56 of sheath 88 and a portion of the void region near the closed end 58. The securing assembly is comprised of protrusions that take the form of "bullets" 84 that protrude from the inner surface 82 of sheath 88 radially inward toward the central axis 60. Given an elongated cylindrical probe having an outer diameter of about 3 mm and an elongated cylindrical sheath 88 having an inner diameter of about 3.3 mm, the bullets protrude about 0.2 mm from the inner surface of sheath 88. Therefore, an unobstructed cylindrical path of about 2.9 mm remains about the sheath's central axis for insertion of the probe. Accordingly, bullets 84 are compliant relative to the probe, so that the bullets 84 compress when the probe is inserted therein to securely grip the probe. The bullets 84 are displaced about the inner surface of the sheath such that an airflow path is maintained between them. In this embodiment, the bullets 84 are made of the same material as sheath 88, an aliphatic thermoplastic polyurethane. Once probe 18 is removed from sheath 88, the annular protrusions 84, e.g., bullets, decompress and return to take substantially their original form. In another form, annular protrusions may be formed along the inner surface of the sheath by having the inner surface be extruded.

Figure 5:
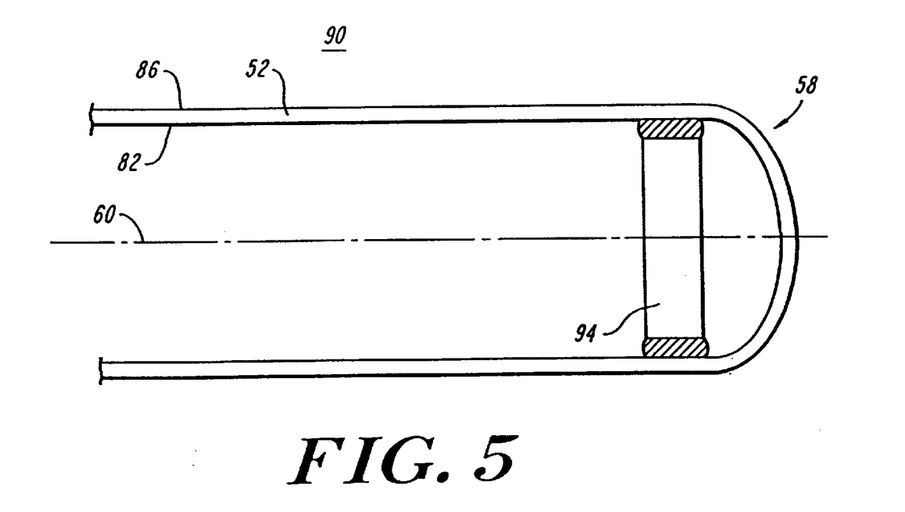
FIG. 5 is a cut-away side view of a sheath, as part of an X-ray emitting kit, having a solid annular ring disposed at the closed end of the inner surface of the sheath.

Referring to FIG. 5, a third embodiment of an X-ray emitting kit includes an improved sheath 90, shown in a cut-away side view. This sheath 90 is substantially similar to the sheath shown in FIGS. 2B–C, except for the placement of an annular ring 94. The annular ring 94 serves as a securing assembly, employing a gripping mechanism, and is compliant with respect to the probe 18. Again, assuming that the probe 18 is an elongated cylinder having an outer diameter of about 3 mm and sheath 90 has an inner diameter of about 3.3 mm, annular ring 94 has a diameter of about 2.9 mm about the central axis and is constructed of an aliphatic thermoplastic polyurethane material. In this embodiment, the annular ring 94 is positioned within the sheath 90 near the closed end 58 and integral with the sheath's inner surface 82. Because annular ring 94 is positioned near the closed end 58 of sheath 90, the annular ring 94 may be a substantially solid ring which allows the probe to be inserted therein without causing a significant amount of air to be trapped within the void region of the sheath 90. When probe 18 is inserted within sheath 90, annular ring 94 forces air present in the void region of sheath 90 to be pushed toward the open end of the sheath, within the air gap realized between the 3.3 mm diameter sheath and 3 mm probe, and away from closed end 58. Once probe 18 is removed from sheath 90, annular ring 94 decompresses and substantially retakes its original form.

While various embodiments of the sheath have been shown, those skilled in the art will appreciate that the annular protrusions can take other forms without departing from the scope of the present invention. For example, radial cuts, or slits, could be made in any of the annular ring securing assemblies discussed herein which separate as the probe is inserted to accommodate the flow of air from the sheath. Additionally, other means could be used to allow air to escape from the sheath as the tube is being inserted therein. For example, a one-way air valve could be positioned proximate to the open end of the sheath to allow air to flow from the sheath, despite the presence of a securing assembly annular ring proximate to the flange which would otherwise trap air in the void region.

Figure 6A:
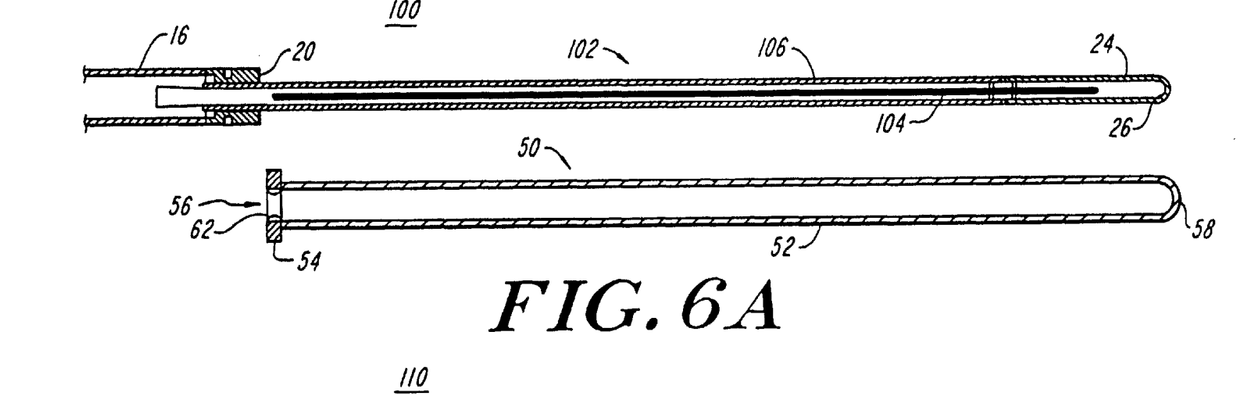
FIGS. 6A–6C are various embodiments of an improved probe, of an X-ray treatment kit, having air channels formed therein.
Figure 6B:
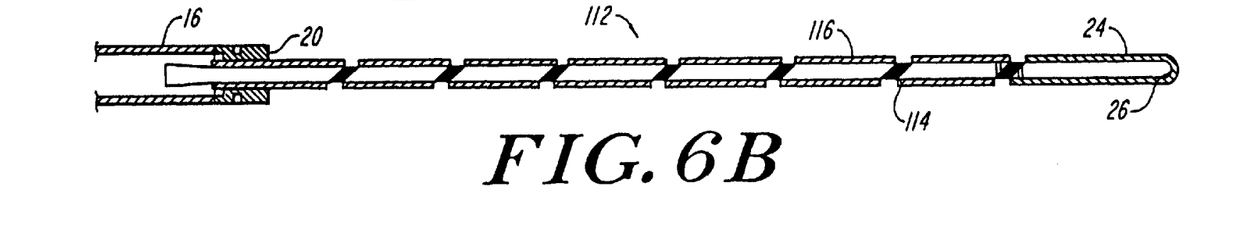
Figure 6C:
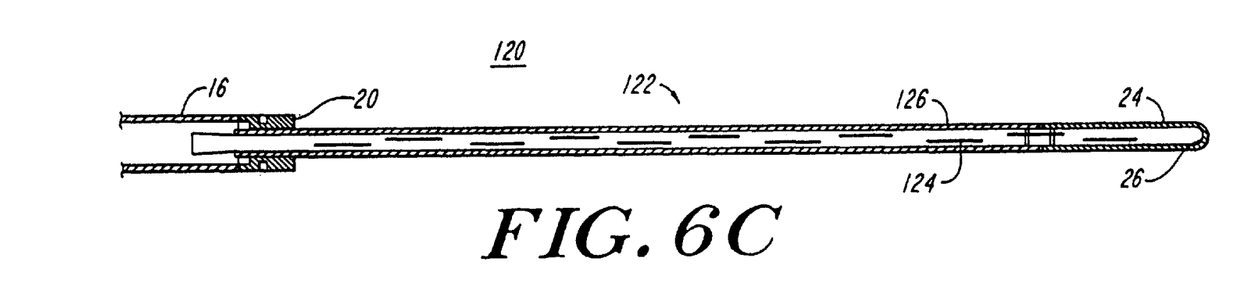

Referring to FIGS. 6A–C, the present invention is also embodied in X-ray emitting kits comprising an improved probe and a typical sheath. That is, various types of probes are shown that provide an airflow path between the sheath and probe, rather than the sheath providing the airflow path. Therefore, if the probe provides an airflow path, the sheath need not also provide one. In such a case, the prior art sheath of FIGS. 2B–C may be used in the kit.

Referring to FIG. 6A, an X-ray emitting kit 100 is shown having an improved probe 102 which provides an airflow path for the escape of air present within the void region of typical sheath 50 (also shown in FIGS. 2B and 2C) as a probe is being inserted therein. As is shown in the figure, sheath 50 includes an annular ring 62 proximate to flange 54 and displaced within the void region of the sheath and integral with the sheath's inner surface. The annular ring 62 is a solid compliant ring that has a inner radial dimension which is slightly less than that of probe 102. As a result, the annular ring 62 grips probe 102 as the probe is inserted therein. Probe 102, shown in a cross sectional view, is secured within a shoulder 16 by an adapted bushing 20 at one end and has a target cap 24 at the other end, preferably a Be cap. The probe includes an elongated cylindrical tubular body 106 that is about 10–16 cm in length. As with the probe of FIGS. 1 and 2A, a target element 26 resides within Be cap 24 and is made of beryllium and coated with a thin film having a high z-element, such as gold. The inner diameter of probe 102 is about 2 mm and the outer diameter is about 3 mm. In this embodiment, an elongated air channel 104 is formed along the surface of probe body 106. In order to effectively provide an airflow path, the channel 104 extends from approximately the bushing 20 to about the target end 24 of probe 102. The depth of channel 104 must sufficient to allow the escape of air, but must not obstruct or otherwise adversely influence the path of electrons within the probe 102.

Referring to FIGS. 6B and 6C, other X-ray emitting kit embodiments 110, 120 are shown which include improved probes 112, 122, wherein each probe provides an airflow path along a substantial length of the tubular body of the probe. Therefore, as with probe 102 of FIG. 6A, these probes may be used with the typical sheath 50 of FIGS. 2B and 2C, wherein a solid annular ring 62 is disposed at the closed end 58 of sheath 50 for gripping the probe. In FIG. 6B, the airflow path takes the form of a continuous spiral airflow path 114 formed within tubular body 116 of probe 112. In FIG. 6C, the airflow path formed within the tubular body 126 of probe 122 takes the form of a plurality of shorter mini air channels 124, rather than a single elongated air channel formed within the probe body. The mini channels 124 formed within the probe body 126 are distributed about the length of the probe 122 to provide an airflow path for substantially the same length of the probe as the single channels 104, 114 of FIGS. 6A and 6B. In another form, the probe may have a pitted or irregular surface for a substantial portion of its length, such that air channels are formed within the probe surface.

The invention may be embodied in other specific forms without departing from the spirit or central characteristics thereof. The present embodiments are therefore to be considered in all respects as illustrative and not restrictive, the scope of the invention being indicated by appending claims rather than by the foregoing description, and all changes that come within the meaning and range of equivalency of the claims are therefore intended to be embraced therein.

What is claimed is:

1. An X-ray treatment kit comprising:
   an elongated X-ray emitter tube; and
   a sheath, comprising:
      an elongated body extending along a central axis and having an elongated central void region extending along the central axis between a closed end and an open end of said body, said open end being adapted to receive said emitting tube, said body having an inner surface and a biocompatible outer surface; and
      a securing assembly positioned within said void region for frictionally engaging said emitting tube;
   a means for defining an airflow path within said body and external to said central void region, said airflow path extending from a portion of said central void region near said closed end and extending past said securing assembly to said open end.

2. The X-ray treatment kit of claim 1 wherein sheath body is made from polyurethane.

3. The X-ray treatment kit of claim 1 wherein the airflow path is maintained by a depression within the emitter tube and extending along a substantial length thereof.

4. The X-ray treatment kit of claim 1 wherein the airflow path is maintained by said sheath.

5. The X-ray treatment kit of claim 4 wherein the airflow path is maintained by a one-way valve near the open end of said sheath.

6. The X-ray treatment kit of claim 1 wherein the airflow path is maintained by the securing assembly.

7. The X-ray treatment kit of claim 6 wherein the securing assembly is disposed within the central void region near the closed end of the body, projecting inwardly from the inner surface toward the central axis, and is relatively compliant with respect to the emitting tube.

8. The X-ray treatment kit of claim 6 wherein the securing assembly is disposed within the central void region and is comprised of a plurality of grip surfaces protruding inwardly from the inner surface, said grip surfaces being relatively compliant with respect to the emitting tube.

9. The X-ray treatment kit of claim 8 wherein the grip surfaces are disposed proximate to the open end of the body.

10. The X-ray treatment kit of claim 6 wherein the securing assembly is an annular protrusion having air shunts formed from cutaway sections within the annular protrusion.

11. The X-ray treatment kit of claim 10 wherein the annular protrusion is disposed proximate to the open end of the body.

* * * * *